United States Patent
Motz et al.

(10) Patent No.: US 9,789,218 B2
(45) Date of Patent: Oct. 17, 2017

(54) STERILE STATUS INDICATOR BY MEANS OF PHASE CHANGE

(71) Applicant: Aesculap AG, Tuttlingen (DE)

(72) Inventors: Corvin Motz, Pfullendorf (DE); Gerold Zieris, Mühlheim (DE); Joachim Amann, Mühlingen-Zoznegg (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 14/778,793

(22) PCT Filed: May 6, 2014

(86) PCT No.: PCT/EP2014/059242
§ 371 (c)(1),
(2) Date: Sep. 21, 2015

(87) PCT Pub. No.: WO2014/180849
PCT Pub. Date: Nov. 13, 2014

(65) Prior Publication Data
US 2016/0045630 A1    Feb. 18, 2016

(30) Foreign Application Priority Data
May 7, 2013 (DE) .................. 10 2013 208 332

(51) Int. Cl.
*G01N 31/22* (2006.01)
*A61L 2/28* (2006.01)
(Continued)

(52) U.S. Cl.
CPC .............. *A61L 2/28* (2013.01); *F28D 20/028* (2013.01); *G01N 31/226* (2013.01); *F24J 1/00* (2013.01);
(Continued)

(58) Field of Classification Search
USPC .......................................... 422/420
See application file for complete search history.

(56) References Cited

U.S. PATENT DOCUMENTS 3,859,856 A * 1/1975 Keele ..................... G01K 11/06
116/207
4,150,572 A * 4/1979 Lindquist ............... G01K 11/06
116/207

(Continued)

FOREIGN PATENT DOCUMENTS

| CN | 86104764 | 1/1988 |
|---|---|---|
| CN | 1034393 | 8/1989 |

(Continued)

OTHER PUBLICATIONS

German Search Report for German Application No. 10 2013 208 332.7 dated Mar. 18, 2014, including partial translation.

(Continued)

*Primary Examiner* — Jill Warden
*Assistant Examiner* — Brittany Fisher
(74) *Attorney, Agent, or Firm* — RatnerPrestia

(57) ABSTRACT

A phase change material is used for the production of a sterile state indication means for a sterilization container. A sterile state indication means for a sterilization container includes a fluid-tight case containing a phase change material. In this assembly, the case wall of the case includes at least one transparent zone and an activator which can be actuated in order to release an activation energy and/or crystallization seeds. The activator is in contact with the phase change material. Further, a sterilization container includes a container trough and a container lid, including a sterile state indication means. The sterile state indication means is provided either on the container trough or on the container lid, and the activator, in the closed state of the
(Continued)

sterilization container, is in direct or indirect connection with the respectively other element among container trough and container lid.

8 Claims, 2 Drawing Sheets

(51) Int. Cl.
    *F28D 20/02*         (2006.01)
    *G01N 33/52*        (2006.01)
    *F24J 1/00*          (2006.01)
    *F28D 21/00*        (2006.01)

(52) U.S. Cl.
    CPC ....... *F28D 2021/005* (2013.01); *Y02E 60/145* (2013.01)

(56) References Cited

U.S. PATENT DOCUMENTS

| | | | |
|---|---|---|---|
| 4,448,548 A * | 5/1984 | Foley | G01N 31/226 252/408.1 |
| 5,087,508 A | 2/1992 | Beck | |
| 5,158,363 A * | 10/1992 | Speelman | A61L 2/28 116/207 |
| 5,378,430 A * | 1/1995 | Nieves | A61L 2/28 116/207 |
| 5,602,804 A * | 2/1997 | Haas | G01K 3/04 116/206 |
| 5,709,472 A * | 1/1998 | Prusik | G01K 3/04 116/219 |
| 6,108,489 A * | 8/2000 | Frohlich | A47J 36/2494 126/263.01 |
| 2002/0022246 A1 * | 2/2002 | Lin | A61L 2/208 436/1 |
| 2003/0211618 A1 | 11/2003 | Patel | |
| 2009/0047176 A1 * | 2/2009 | Cregger | A61L 2/28 422/28 |
| 2011/0275159 A1 * | 11/2011 | Landgrebe | A61L 2/28 436/1 |
| 2012/0034131 A1 * | 2/2012 | Rubinsky | A23B 4/012 422/22 |
| 2012/0095605 A1 | 4/2012 | Tran | |
| 2012/0156090 A1 * | 6/2012 | Dane | C12Q 1/22 422/1 |

FOREIGN PATENT DOCUMENTS

| | | |
|---|---|---|
| CN | 2885165 | 4/2007 |
| CN | 101186806 | 5/2008 |
| JP | 07171206 | 7/1995 |
| JP | 2010505490 | 2/2010 |
| WO | 8908228 | 9/1989 |
| WO | 0186289 | 11/2001 |
| WO | 2008041146 | 4/2008 |
| WO | 2012082289 | 6/2012 |
| WO | 2012135694 | 10/2012 |

OTHER PUBLICATIONS

Hornberger, R. et al., "Phase-change materials provide simple and reliable temperature indications," Welding Design (Oct. 19, 2007) URL: http://weldingdesign.com/archive/phase-change-materials-provide-simple-and-reliable-temperature-indications [retrieved Aug. 20, 2015].

International Search Report for International Application No. PCT/EP2014/059242 dated Jul. 31, 2014.

Oberpaul, Petra, "Latent heat accumulators—functional principle and fields of use," 2002, including English translation.

Japanese Office Action for Japanese Application No. 2016509506, dated May 31, 2016 with translation, 8 pages.

Chinese Office Action for Chinese Application No. 201480014459.5, dated May 27, 2016 with translation, 15 pages.

Chinese Office Action for Chinese Application No. 201480014459.5, dated Dec. 1, 2016 with translation, 18 pages.

Disinfection, Disinsection and Deratization Manual, Mar. 31, 1980, 9 pages.

* cited by examiner

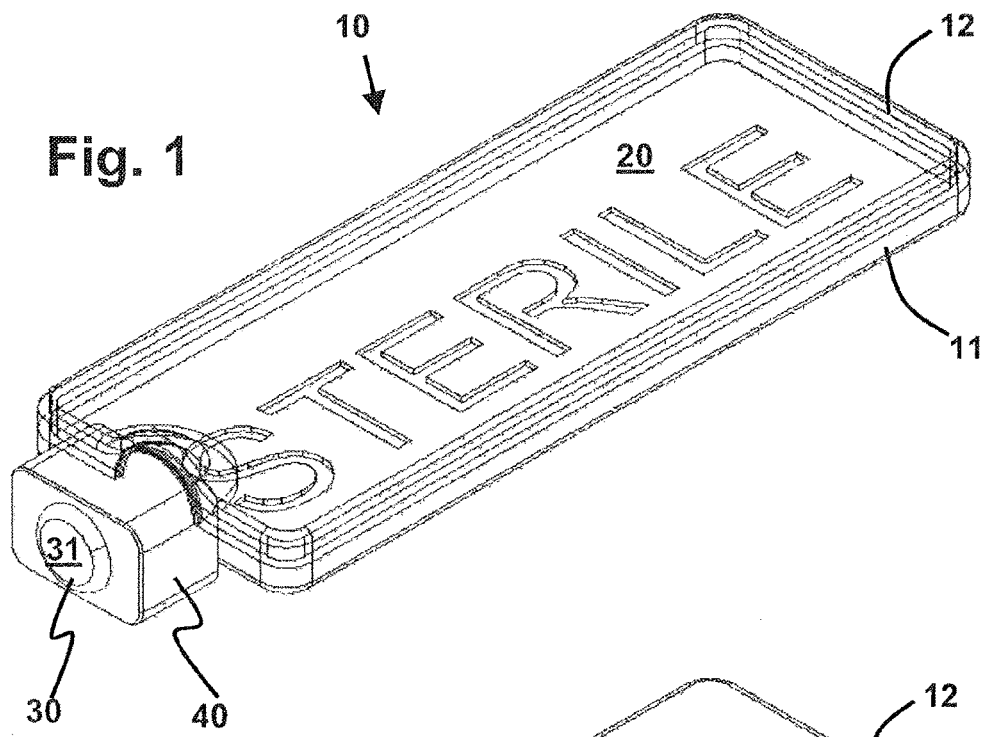
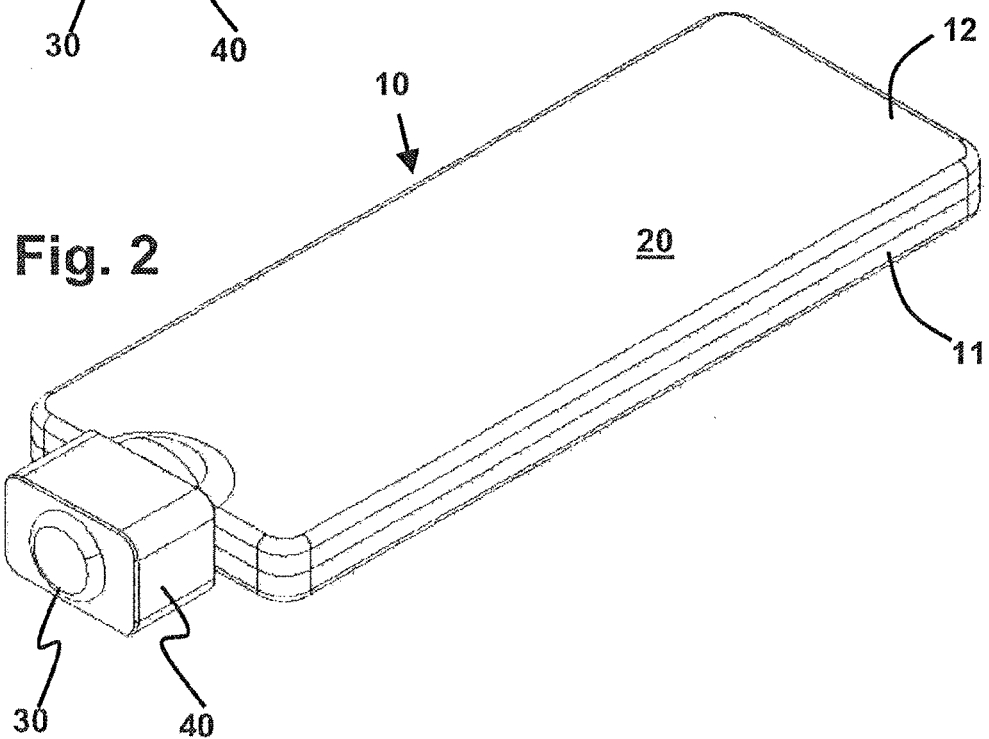

STERILE STATUS INDICATOR BY MEANS OF PHASE CHANGE

RELATED APPLICATIONS

This application is the U.S. National Phase entry of International Application No. PCT/EP2014/059242, filed May 6, 2014, which claims the benefit of priority of German Application No. DE 10 2013 208 332.7, filed May 7, 2013. The contents of International Application No. PCT/EP2014/059242 and German Application No. DE 10 2013 208 332.7 are incorporated by reference herein in their entirety.

FIELD

The present invention relates to the use of a phase change material for the production of a sterile state indication means for a sterilization container as well as to a sterilization container comprising a sterile state indication means based on said principle.

BACKGROUND

Numerous forms of sterile state indication means or sterile state indicators for sterilization containers are known in prior art. Such indicators serve to signalize the staff if a sterilization container has already been sterilized or not. Said sterile state indicators respond to heat and/or vapor and change their color during the sterilization process. Subsequent to the sterilization process, the staff is able to determine on the basis of the color of the indicator spot that the content of the container is sterile. The indicator spots are attached either on labeling cardboard or on a container seal. If the indicator spot is provided on a labeling cardboard, however, there is the risk that such a labeling cardboard, after the use of a container and its content, is not removed and replaced by a new labeling cardboard; instead, the labeling cardboard may remain on the container and in this way erroneously indicate that the container together with its content has been freshly sterilized.

If the indicator spot is on a container seal which has to be destroyed for opening the container, it cannot happen by accident that the old indicator spot remains on the container. With some container seals, however, it is difficult to clearly see if the seal has already been destroyed. In this case, an old seal might be attached to a container and thus indicate in erroneous fashion that the content of the container is sterile. In both cases, however, the indicator has to be replaced after every use, involving an extra working step and the stockage of the indicators or the seals along with indicators.

Other sterile state indication systems work with bimetallic springs or shape memory metals which are deformed during the sterilization process mostly against a regular spiral spring and displace a display element in order to lock it in place under pretension of the regular spiral spring. If the container is opened, the locking of the display element is released and it returns to a position which does not indicate the sterile state any longer. However, these systems have the disadvantage that they require a very complex structure which calls for many individual movable parts. Moreover, these systems need a considerable construction volume which reduces the usable volume of the container. This results in considerable manufacturing costs. Components made up of shape memory metals are also very expensive. On the other hand, these systems can be used in reversible fashion and do not have to be replaced before each sterilization process as is the case with the previously described indicator spots.

In the prior art, so-called phase change materials (PCM) are also known. Phase change materials are usually used for latent heat accumulators. An insight into the basics of latent heat accumulators and phase change materials can be found in the paper "Latent heat accumulators—functional principle and fields of use" by Petra Oberpaul, 2002. In said paper, solar energy production, housebuilding or the automotive industry are mentioned as application areas, for example. Further, a distinction is made between three classes of phase change materials, namely eutectic water-salt solutions, organic phase change materials and salt hydrates. Eutectic water-salt solutions are mainly used for cold storage purposes. Paraffins (long-chain hydrocarbons) and sugar alcohols such as erythritol, mannitol and sorbitol belong to the organic phase change materials. In the intended temperature range between room temperature and the sterilization temperature, salt hydrates are the favorite alternatives. Examples for salt hydrates include calcium chloride hexahydrate, sodium sulfate decahydrate, disodium hydrogen phosphate dodecahydrate, disodium thiosulfate pentahydrate, sodium acetate trihydrate, barium hydroxide octahydrate and a mixture of magnesium hydrate hexahydrate and lithium nitrate.

SUMMARY

It is therefore the object of the present invention to provide a reversible sterile state indication means for a sterilization container, which is of simple construction, inexpensive, space-saving and reversible. The object of the present invention is achieved by the use of a phase change material for the production of a sterile state indication means, a sterile state indication means and a sterilization container as described herein.

According to a first aspect of the present invention, a phase change material is used for the production of a sterile state indication means for a sterilization container. A phase change material is a material which transforms from the solid phase to the liquid phase at a defined temperature, i.e. is melted and/or dissolved, and absorbs energy during this process. In the solid phase, phase change materials have a crystalline structure and hence are substantially opaque. In the liquid phase, however, the phase change materials are clear and well transparent. This is why in the solid phase a phase change material is able to block the view on a display element which shows that the object on which the phase change material and the display are provided is sterile. In the liquid phase, however, the phase change material unblocks the view on the display and shows the viewer in this way that the object and its content, if any, are sterile. The user is also able to detect the sterile or unsterile state of the object directly on the basis of the fact whether the phase change material is liquid or solid, either visually or in tactile fashion, if the material is stored in a soft case. Hence, a display is not strictly necessary. It is also not imperative that the case comprises a transparent zone.

In addition, the phase change materials have a further important property: They can be strongly supercooled in the liquid phase, i.e. below the freezing or solidification point, without leaving the liquid phase spontaneously and getting solidified or frozen. In order to crystallize starting from the supercooled state, i.e. to freeze and/or to solidify, the phase change material has to be cooled down to below a crystallization temperature which is far below the freezing temperature, it is necessary to add crystallization seeds and/or the crystallization process has to be activated by means of a pressure impulse or a pressure wave or any other energy input such as an electric spark. This means that the phase change material after liquefaction is able to remain in the liquid state for a long time and at a temperature which is significantly below the melting temperature of the material, and then freezes by activating the crystallization; in this process, the material emits heat and becomes turbid at the same time. If the crystallization has been initiated, all the phase change material freezes to the core as in a chain reaction. On the other hand, the phase change material needs a heat input above the melting temperature (equal to the freezing temperature) for a certain time in order to become completely liquefied. The required time depends on the amount of the phase change material and the employed temperature.

A sterilization process in the medical sector, such as with a medical sterilization container which is used in a hospital and is filled with instruments, takes place in a temperature range from room temperature to at least 100° C. The room temperature may differ in different regions of the world. It may also happen that the sterilization of the instruments is not carried out at the place where they are used. In this case, it may also happen that the phase change material during transport is exposed to temperatures which are significantly below room temperature, possibly even below 0° C. There are phase change materials which have a crystallization temperature of approximately −20° C. On the other hand, there are phase change materials such as D-mannitol which have a melting point of approximately 160° C. which is significantly above the temperatures which are reached with a conventional sterilization process by use of vapor sterilization in a hospital.

This means that the melting point or the melting temperature of the phase change material has to be above room temperature. In the ideal case, it is somewhat beyond it so that the phase change material is prevented from being unintentionally liquefied, for instance by sun exposure or the heat of a lighting device, by a tactile contact (body temperature approximately 37° C.), by an inadvertent open steam exposure (e.g. by vapor escaping from a dishwasher), etc. This could have the effect that an unsterile container together with its content is unintentionally deemed to be sterile, as the phase change material liquefies without an appropriate sterilization process having been performed. The crystallization temperature, however, has to be below the minimum room temperature in order to prevent that a sterile container is unintentionally considered as an unsterile one, as the phase change material conceals the display for the sterile state after a regular sterilization process, without the content of the container having become unsterile in reality (for instance by opening the container). Finally, the melting temperature has to be below the maximum temperature which is reached in a conventional sterilization process, as otherwise there will be no liquefaction of the phase change material during the sterilization process and the container always remains marked as unsterile. It is also important to take care that the heat input into the phase change material during the sterilization process is sufficiently high in order to liquefy the entire phase change material, as any phase change material which has not been liquefied would serve as crystallization seed for the already liquefied phase change material in case of cooling, with the effect that the latter would freeze at once during cooling and hence not reach the supercooled state.

TABLE 1

Salt hydrates and their melting temperature

| Salt hydrate (chemical formula) | Melting temperature |
|---|---|
| Calcium chloride hexahydrate ($CaCl_2 \cdot 6H_2O$) | 27° C. |
| Sodium sulfate decahydrate ($Na_2SO_4 \cdot 10H_2O$) | 32° C. |
| Disodium hydrogen phosphate dodecahydrate ($Na_2HPO_4 \cdot 12H_2O$) | 35° C. |
| Disodium thiosulfate pentahydrate ($Na_2S_2O_3 \cdot 5H_2O$) | 48° C. |
| Sodium acetate trihydrate ($NaCH_3COO \cdot 3H_2O$) | 58° C. |
| Magnesium hydrate hexahydrate lithium nitrate ($Mg(NO_3)_2 \cdot 6H_2O/Li(NO_3)$) | 72° C. |
| Barium hydroxide octahydrate ($Ba(OH)_2 \cdot 8H_2O$) | 78° C. |

According to an advantageous embodiment of the first aspect of the present invention, the phase change material has a melting temperature in a temperature range from 25° C. to 100° C., preferably from 30° C. to 80° C., more preferably from 35° C. to 75° C. and most preferably from 40° C. to 60° C. In the temperature range which is named first, a somewhat increased room temperature—which may be reached for instance in warm summer days—has been taken into consideration for the lower limit so that the employed phase change material cannot liquefy unintentionally. The upper limit is selected such that a complete liquefaction of the phase change material is reliably ensured with any sterilization process currently used in hospitals. The second and third temperature ranges mentioned above gradually increase the safety with respect to an undesired liquefaction of the phase change material on the one hand, and on the other hand they prevent the staff from being injured (burnt) on the freshly sterilized container if it is taken out of the sterilizer after a sterilization process. The last-mentioned range additionally enables the staff to remove the container from the sterilizer in unprotected manner. It has also to be taken into consideration here that any action of opening the container or its closure results in a crystallization of the phase change material. In doing so, the material reaches its melting temperature and maintains it due to the relatively large energy density of the phase change material for a relatively long time before it cools down to room temperature. Therefore, with high melting temperatures, there is a risk of injury (e.g. burn) for the staff even if the container has already cooled down. Due to the crystallization, the container is locally warmed or heated up to the melting temperature. Thus, a lower melting temperature increases the safety for the staff during use of the container. Moreover, a low melting temperature considerably reduces the time until the phase change material is cooled down to room temperature after crystallization. The phase change material may contain in particular sodium acetate trihydrate and/or disodium thiosulfate pentahydrate. However, there are also organic phase change materials such as D-sorbitol the melting temperature of which is in a comfortable and safe range (approximately 70° C.). It is also possible, however, to prevent the staff from being injured during or shortly after crystallization of the phase change material by constructional measures by conducting the heat away from any possible zones of contact with the staff, in that the amount of the phase change material is kept as small as possible and/or in that the phase change material is shielded and/or isolated in terms of a direct contact.

According to a second aspect of the present invention, a sterile state indication means is disclosed for a sterilization container comprising a fluid-tight case containing a phase change material. The case wall of the case comprises at least one transparent zone so that it is possible to look into the container from outside. The sterile state indication means further comprises an activator which can be actuated in order to release an activation energy and/or crystallization seeds. The activator is in contact with the phase change material and any actuation of the activator supplies the supercooled and liquid phase change material with activation energy and/or crystallization seeds, whereupon it freezes or solidifies. During the freezing or solidification of the phase change material, heat is released; above all, the phase change material is converted from a clear (transparent) liquid to an opaque (non-transparent) solid body. Said conversion may partially occur by way of a mixed state in which a part of the phase change material is still in the liquid phase which is present in an already solidified crystal lattice. In this intermediate state, the phase change material is already opaque. In this basic embodiment, a user of the sterile state indication means is able to perceive through the transparent zone of the case wall if the case houses a clear (transparent) liquid or an opaque solid body. The intermediate state can also be detected. Further details concerning the intermediate state can be taken from the prior art.

According to an advantageous embodiment of the second aspect of the present invention, a labeling and/or color marking is provided on and/or in the fluid-tight case in such a manner that it faces the transparent zone of the case wall at least in certain areas. This embodiment has the advantage that the user is not required to detect the transparency or non-transparency of the phase change material itself; rather, he can utilize the transparency of the liquid material and make out a display which is provided in the case or on its inner wall. For a user, it is easier to detect if a color marking or a labeling is visible or not, than to detect if a medium in a case is transparent or opaque. In particular a combination of a color marking and a labeling such as the lettering "STERILE" in black letters on a green surface should be easily identifiable for a user through the liquid and hence transparent or clear phase change material. If such a marking cannot be seen, the phase change material is not in the liquid phase but in the solid phase or a transition state.

According to another advantageous embodiment of the second aspect of the present invention, the labeling and/or color marking is provided on an inner side of the case wall and is preferably arranged so as to be opposite to the transparent zone of the case wall. In this case, the number of parts can be kept low. Ideally, the case consists of a transparent front half shell, a rear half shell with a substantially mirror-symmetric shape and a marking and/or labeling on its inner wall. The activator is provided in a recess which is disposed at a place in a contact zone of the two half shells of the case. A case of this type can be produced and processed in an easy way, in short time, at low cost and in small sizes. It is further preferred that the zone of the case wall comprising the labeling and/or color marking, and/or the transparent zone of the case wall are formed so as to be substantially planar and/or curved. With such a design, a magnifier effect is made use of, which arises if the phase change material is in the liquid phase. This way, it is even more easier for the user to discern the marking and/or labeling if the phase change material is liquid.

According to a further advantageous embodiment of the second aspect of the present invention, the activator comprises a spring element which is according to the clicker principle and preferably arranged in the case wall of the fluid-tight case. In the ideal case, the spring element has a rotationally symmetrical shape comprising a central bulge. In this way, the spring element may be formed as a part of the case wall and arranged between two essential half shells of the case. The edge of the spring element may be firmly clamped by the case wall, as the edge of the spring element during activation will not be deformed or only to a negligible extent. The central bulge, however, is able to move into the container or out of it and in so doing initiate the phase change of the phase change material from liquid to solid.

If the spring element triggers the crystallization of the phase change material by providing crystallization seeds, these crystallization seeds are according to the current state of the art no fragments or the like of the spring element. Rather, it can be assumed that the surface of the spring element comprises minute furrows and/or gaps in which smallest amounts of crystallized material are enclosed during the bending of the material and are separated in this way from the rest of the phase change material if the spring element returns to its initial position. Said crystallization seeds which are trapped in the spring element will not be liquefied even if the remainder of the phase change material is liquefied by a corresponding supply of heat. This may be due to the fact that the volume increases during the liquefaction of the phase change material, for example. This may be prevented in the spring element for instance by the prevailing pressure conditions. If the spring element is now again flexed or bent, the zones of the solidified phase change material which have been separated up to now come into contact with the remaining, liquid phase change material and the liquid phase change material crystallizes to the core. Regarding the way of operation of the sterile state indication means, the trigger mechanism does not play any role in detail. Fragments of the spring element are also able to trigger the crystallization of the liquid phase change material. Apart from that, there is also some evidence that the pressure wave (sound wave of the cracking process) brought about by the clicker effect is sufficient for starting the crystallization process. The crystallization can be reliably and reproducibly triggered by a spring element which utilizes the clicker effect. The widespread hand-warming units including or made of a phase change material all use an activator according to this principle.

According to a further advantageous embodiment of the second aspect of the present invention, the activator comprises a piezo element which is adapted to deliver the produced electric energy to the phase change material. Apart from providing the crystallization seeds and the introduction of pressure waves and/or sound waves into the phase change material, the crystallization may also be triggered by an electric impulse. A particular simple means of providing such an electric impulse is to use a piezo element, as it is employed in similar fashion in gas lighters. Such an activator is inexpensive, has a small size and can be processed without any problems.

According to another advantageous embodiment of the second aspect of the present invention, the sterile state indication means is provided either on the container trough or on the container lid, and the activator, in the closed state of the sterilization container, is in direct or indirect connection with the respectively other element among container trough and container lid. With such a design, the number of parts can be minimized and it can be ensured that during opening the sterilization container the activator is triggered or actuated and hence the crystallization of the liquid phase change material is initiated. Here, opening the sterilization container means that the lid is lifted off from the trough of the sterilization container or removed from it.

According to a still further advantageous embodiment of the second aspect of the present invention, the container lid or the container trough comprises a pivotable closure lug, and the activator, in the closed state of the closure lug, is in direct or indirect connection with the closure lug. Here, it does not matter if the closure lug is pivotally provided on the container lid or container trough. With such an embodiment, the process of opening the sterilization container and hence initiating the crystallization of the liquid phase change material can already be effected if the closure lug is moved out of its closure position. To this end, the activator is in connection with the closure lug and is triggered upon its actuation or movement.

According to a further advantageous embodiment of the second aspect of the present invention, the activator is a spring element which is realized according to the clicker principle and is preferably arranged in the case wall of the fluid-tight case, the spring element preferably being in a pretensioned state in the closed state of the closure lug and/or of the sterilization container. In this way, even a very slow and cautious way of opening the sterilization container triggers the crystallization of the liquid phase change material in that the spring element relaxes abruptly if the space required therefore is made available. Depending on which part the sterile state indication means is provided, the container lid, the container trough or the closure lug on one of the two afore-mentioned parts will be moved away from the spring element and provides the space required for the relaxation of the spring element. During relaxation of the spring element, a pressure wave is induced on the one hand, initiating a crystallization of the liquid phase change material; on the other hand, minute crystallization seeds enclosed in the spring element are released which also bring about a crystallization of the liquid phase change material. The specific processes for initiating the crystallization of the phase change material are described in the previously cited prior art.

According to a still further embodiment of the second aspect of the present invention, the spring element, in the closed state of the closure lug, is in connection with the closure lug and in particular with a lateral surface of the closure lug by means of a preferably elastically supported actuation element, so that it will be moved away from the case upon actuation of the closure lug. This allows to ensure that the actuation element does not get stuck even after a longer period of storing the sterilization container in the sterilized state which would entail in a defective manner that the crystallization of the liquid phase change material is not triggered.

BRIEF DESCRIPTION OF THE DRAWING FIGURES

Further advantages and features of the invention are apparent to a person skilled in the art from the attached Figures and the detailed description of the exemplary embodiments.

FIG. 1 shows an isometric view of the sterile state indication means according to the preferred exemplary embodiment in the sterile state;

FIG. 2 shows an isometric view of the sterile state indication means according to the preferred exemplary embodiment in the unsterile state;

DETAILED DESCRIPTION

Figure 3:
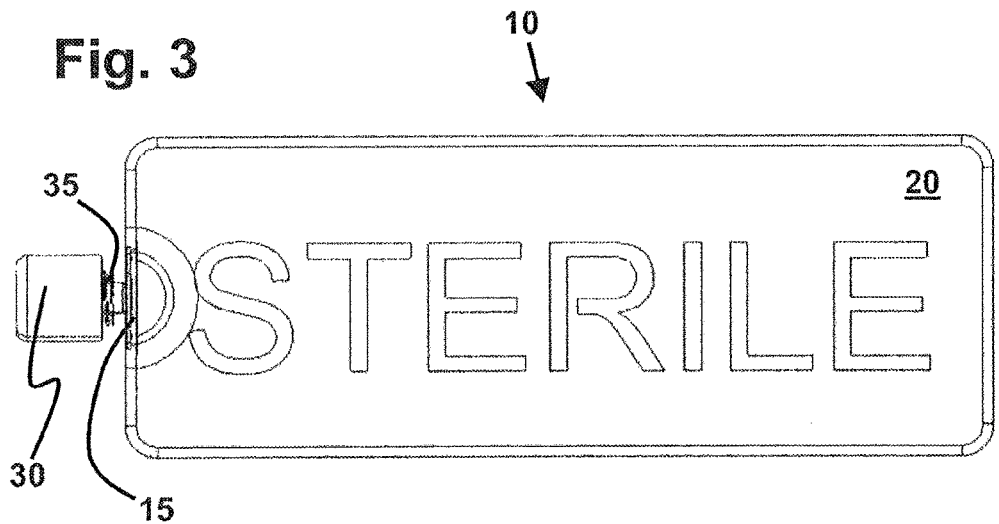
FIG. 3 shows a view of the sterile state indication means according to the preferred exemplary embodiment in the sterile state as seen from the front.

A preferred exemplary embodiment of the present invention will be described in detail below with reference to Figures.

FIG. 1 shows a sterile state indication means for a sterilization container (not shown) comprising a fluid-tight case 10 which holds a phase change material 20. The case 10 is formed from two shell-like parts 11 and 12; here, part 11 forms the rear wall 11 of the case 10 where the case is fastened to the trough of the sterilization container, and part 12 forms the front wall 12 facing the user. The front wall 12 is made of transparent plastics and the rear wall 11 is made of non-transparent plastics. The front side of the rear wall 11 is provided with the lettering "STERILE", for instance as a black lettering on a light green background. If the phase change material 20 is liquid, said lettering "STERILE" is legible for the user. Provided between the rear wall 11 and the front wall 12 is a round metal platelet 15 which is curved in the relaxed state and hence constitutes a so-called clicker-type device. The rear wall 11, the front wall 12 and the metal platelet 15 enclose the phase change material 20 in fluid-tight manner. In addition, the phase change material completely fills the case 10. As the phase change material expands during crystallization, the case is provided with such an elasticity that it is not destroyed by such volume increase. As an alternative, the case may be provided with a section which serves for compensating the volume increase, for instance a plastic bag. In order to be able to give the case 10 a substantially thin design without having to form the metal platelet 15 too small, the rear wall 11 and the front wall 12 comprise zones 14 (not shown for the rear wall) which will be bulged.

In the pretensioned state, the metal platelet 15 is substantially planar and in contact with an actuation element 30. The actuation element 30 is slidably supported in a supporting element 40 in such a manner that it can be moved away from the metal platelet 15 and toward it. A spring 35 is supported on one side by the supporting element 40 and on the other side by the actuation element 30 and urges the actuation element 30 away from the metal platelet 15.

The end 32 of the actuation element 30 biases the metal platelet 15 toward the interior of the case, as a closure lug 50 of the sterilization container, which is pivotally attached on the container lid, urges the other end 31 toward the case 10 against the force of the spring 35. In the view illustrated in FIG. 4, the closure lug 50 is in the closed state. By means of two eye elements 51, 51, the closure lug 50 is pivotally supported on a flap (not shown) on the container lid. Provided in the opening 52 is a protrusion which is arranged on the container trough. In principle, the closure lug 50 corresponds to a closure lug as it is shown in prior art.

Figure 4:
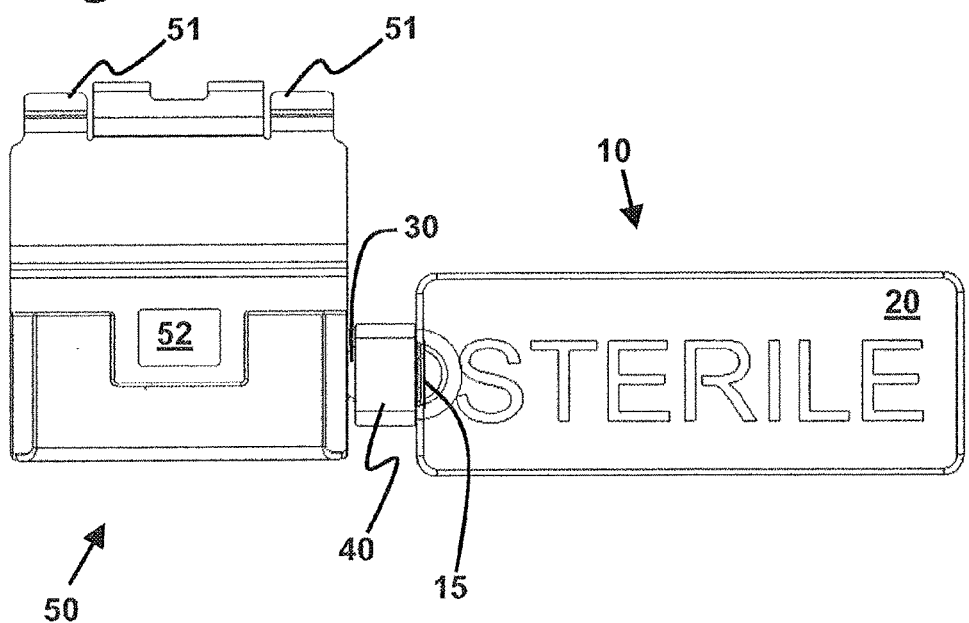
FIG. 4 shows a view of the sterile state indication means according to the preferred exemplary embodiment and a closure lug of a sterilization container in the sterile state as seen from the front.

In FIG. 4, the closure lug 50 is in the closed state and the sterile state indication means indicates that the container is sterile, as the phase change material 20 in the case 10 is liquid. This means that the container, since the last action of closing the closure lug 50, has undergone a sterilization process during which the sterilization container and hence the sterile state indication means were exposed to a specific temperature for a certain time. In the present exemplary embodiment, sodium acetate trihydrate ($NaCH_3COO \cdot 3H_2O$) is provided as the phase change material 20 in the case 10.

The sterilization process reaches far more than 58° C., which corresponds to the melting temperature of sodium acetate trihydrate, and maintains said temperature for a sufficiently long time, so that a complete liquefaction of the sodium acetate trihydrate 20 provided in the case 10 is achieved. The crystallization seeds which are enclosed in minimum notches formed in the metal platelet 15 remain unaffected. After the sterilization process, the container cools down to a temperature below 58° C. due to the lower ambient temperature, and the sodium acetate trihydrate reaches a metastable, supercooled state. In said supercooled state, the sodium acetate trihydrate continues to be liquid and transparent for the time being.

If the content of the sterilization container is required, the container is checked to the effect if it is still sterile. The sterile state indication means clearly shows the lettering "STERILE", so that the user can be sure that the content of the container is sterile. If the closure lug is operated now, the spring 35 urges the actuation element 30 away from the supporting element 50 and the case 10. The pretensioned metal platelet 15 assists this movement and the clicker effect of the metal platelet is triggered. This causes a crystallization of the sodium acetate trihydrate which will become non-transparent within few seconds. From now on, the lettering "STERILE" of the sterile state indication means is no longer visible, as is shown in FIG. 2. The lid of the container can be taken off now and the instruments and/or implants placed in the container trough or in the sieve basket provided therein can be used. After use, the instruments and possibly the implants are put back into the container trough or a sieve basket provided in the container trough and the lid of the container is again attached to the container trough. Subsequently, the closure lug is restored to the closed state so that the sterilization container is correctly closed.

In said process, however, the sodium acetate trihydrate is not supplied with such a high amount of energy that it would be able to liquefy and make the lettering "STERILE" visible again. As the sterile state indication means conceals the lettering "STERILE" at that time, any further potential user will know that the content of the sterilization container is not sterile and must not be used unless the container and its content have been cleaned and notably sterilized.

Even in case of an irradiation with high-power lamps and an increased room temperature, the sodium acetate trihydrate will not be fully liquefied. In the event of an only partial liquefaction of the sodium acetate trihydrate, as it could happen theoretically if a still hot electrode of a TFT apparatus (TFT: Tissue Fusion Technology) would touch the case, the sodium acetate trihydrate automatically crystallizes again if the local temperature falls below the melting temperature.

Numerous modifications and variants to the previously described exemplary embodiments will be apparent to those skilled in the art. In some circumstances, the phase change material may be colored or the front wall 12 of the case 10 may be shaped such that the phase change material and the transparent zone of the case 10 form a kind of magnifier which shows the lettering "STERILE" in enlarged manner and hence improves its legibility.

The invention claimed is:

1. A method for producing a sterilization container comprising the steps of:
   providing a container;
   providing a phase change material that supercools in the liquid phase below the freezing or solidification point of the phase change material; and
   providing a sterile state indication means, the sterile state indication means comprising the phase change material.

2. The method according to claim 1, wherein the phase change material contains sodium acetate trihydrate and/or disodium thiosulfate pentahydrate.

3. A sterile state indication means for a sterilization container comprising:
   a fluid-tight case containing a phase change material, wherein the case wall of the case comprises at least one transparent zone, and
   an activator which can be actuated in order to release an activation energy and/or crystallization seeds, the activator being in contact with the phase change material,
   wherein the phase change material and the transparent zone are adapted to each other such that the phase change material is non-transparent through the transparent zone when it is in a solid state and becomes transparent through the transparent zone when it is in a liquid state, and
   wherein a labeling and/or color marking is provided so as to be opposite the transparent zone of the case wall.

4. The sterile state indication means according to claim 3, wherein
   the labeling and/or color marking is provided on and/or in the fluid-tight case in such a manner that it faces the transparent zone of the case wall at least in parts.

5. The sterile state indication means according to claim 3, wherein
   the activator comprises a spring element, which is realized according to the clicker principle and is arranged in the case wall of the fluid-tight case.

6. The sterile state indication means according to claim 3, wherein
   the activator comprises a piezo element which is adapted to deliver the produced electric energy to the phase change material.

7. A sterilization container comprising a container trough and a container lid, comprising:
   a sterile state indication means comprising:
   a fluid-tight case containing a phase change material, wherein the case wall of the case comprises at least one transparent zone, and
   an activator which can be actuated in order to release an activation energy and/or crystallization seeds, the activator being in contact with the phase change material, wherein the sterile state indication means is provided either on the container trough or on the container lid, and the activator, in the closed state of the sterilization container, is in direct or indirect connection with the respectively other element among container trough and container lid,
   wherein the container lid or the container trough comprises a pivotable closure lug and the activator, in the closed state of the closure lug, is in direct or indirect connection with the closure lug,
   wherein the activator is a spring element which is realized according to the clicker principle and arranged in the case wall of the fluid-tight case, the spring element being in a pretensioned state in the closed state of the closure lug and/or of the sterilization container, and
   wherein the spring element, in the closed state of the closure lug, is in connection with a lateral surface of the closure lug by means of an elastically supported actuation element.

8. A method for producing a sterilization container comprising the steps of:

providing a container; and
providing the sterile state indication means of claim 3.

\* \* \* \* \*